US006621040B1

(12) United States Patent
Perry et al.

(10) Patent No.: US 6,621,040 B1
(45) Date of Patent: Sep. 16, 2003

(54) ULTRASHORT PULSE LASER MACHINING OF METALS AND ALLOYS

(75) Inventors: Michael D. Perry, Livermore, CA (US); Brent C. Stuart, Fremont, CA (US)

(73) Assignee: The Regents of the University of California, Oakland, CA (US)

( * ) Notice: Subject to any disclaimer, the term of this patent is extended or adjusted under 35 U.S.C. 154(b) by 1027 days.

(21) Appl. No.: 08/859,020

(22) Filed: May 20, 1997

Related U.S. Application Data

(63) Continuation-in-part of application No. 08/584,522, filed on Jan. 11, 1996, now Pat. No. 5,720,894.

(51) Int. Cl.⁷ ............................................. B23K 26/36
(52) U.S. Cl. ............................. 219/121.67; 219/121.72
(58) Field of Search ..................... 219/121.6, 121.61, 219/121.68, 121.69, 121.67, 121.7, 121.71, 121.72, 121.85; 216/65

(56) References Cited

U.S. PATENT DOCUMENTS 5,656,186 A * 8/1997 Mourou et al. ......... 219/121.69
5,720,894 A * 2/1998 Neev et al. .................... 216/65
5,736,709 A * 4/1998 Neiheisel ............... 219/121.61

OTHER PUBLICATIONS

Mao et al., "Buffer gas effects on the ablation rates of copper using a pico–second pulsed Nd:YAG laser," Material Research Society Symposium Proceeding, vol. 285, pp. 187–190, Dec. 1992.*
Kautek et al., "Femtosecond pulse laser ablation of metallic, semiconducting, ceramic, and biological materials," SPIE vol. 2207, pp. 600–611, Apr. 1994.*
Preuss et al., "Sub–picosecond UV–laser ablation of Ni films," Applied Physics A, vol. 59, pp. 79–82, Aug. 1994.*
Bostanjoglo et al., "Ablation of metal films by picosecond laser pulses imaged with high–speed electron microscopy," Journal of Applied Physics, vol. 76, No. 5, pp. 3045–3048, Sep. 1994.*
Pronko et al., "Machining of sub–micron holes using a femtosecond laser at 800 nm," Optics Communications vol. 114, pp. 106–110, Jan. 1995.*
Krueger et al., "Femtosecond–pulse laser processing of metallic and semiconducting thin films," SPIE vol. 2403, pp. 436–447, Feb. 1995.*

(List continued on next page.)

Primary Examiner—Samuel M. Heinrich
(74) Attorney, Agent, or Firm—John P. Wooldridge; Alan H. Thompson

(57) ABSTRACT

The invention consists of a method for high precision machining (cutting, drilling, sculpting) of metals and alloys. By using pulses of a duration in the range of 10 femtoseconds to 100 picoseconds, extremely precise machining can be achieved with essentially no heat or shock affected zone. Because the pulses are so short, there is negligible thermal conduction beyond the region removed resulting in negligible thermal stress or shock to the material beyond approximately 0.1–1 micron (dependent upon the particular material) from the laser machined surface. Due to the short duration, the high intensity ($>10^{12}$ W/cm²) associated with the interaction converts the material directly from the solid-state into an ionized plasma. Hydrodynamic expansion of the plasma eliminates the need for any ancillary techniques to remove material and produces extremely high quality machined surfaces with negligible redeposition either within the kerf or on the surface. Since there is negligible heating beyond the depth of material removed, the composition of the remaining material is unaffected by the laser machining process. This enables high precision machining of alloys and even pure metals with no change in grain structure.

11 Claims, 5 Drawing Sheets

OTHER PUBLICATIONS

Preuss et al., "Sub–picosecond UV laser ablation of metals," Applied Physics A, vol. 61, pp. 33–37, Jul. 1995.*

Pronko et al., "Thermophysical effects in laser processing of materials with picosecond and femtosecond pulses," Journal of Applied Physics, vol. 78, No. 10, pp. 6233–6240, Nov. 1995.*

Stuart et al., "Nanosecond–to–femtosecond laser–induced breakdown in dielectrics," Physical Review B, vol. 53, No. 4, pp. 1749–1761, Jan. 1996.*

Garnov et al., "Laser Processing of ceramics and metals by high intense picosecond and nanosecond laser pulses in UV, visible and IR range of spectrum," SPIE vol. 2703, pp. 442–456, Feb. 1996.*

* cited by examiner

- 5.7 J/cm², 17,400 pulses, 1mm
  = 10 nm·cm²/J·pulse

ULTRASHORT PULSE LASER MACHINING OF METALS AND ALLOYS

RELATED APPLICATIONS

This application is a Continuation-in-part of U.S. patent application Ser. No. 08/584,522, filed Jan. 11, 1996, now U.S. Pat. No. 5,720,894, titled "Ultrashort Pulse High Repetition Rate Laser System for Material Processing".

The United States Government has rights in this invention pursuant to Contract No. W-7405-ENG48 between the United States Department of Energy and the University of California for the operation of Lawrence Livermore National Laboratory.

BACKGROUND OF THE INVENTION

1. Field of the Invention

The present invention relates to the use of lasers to cut metals, and more specifically, it relates to the use of ultrashort laser pulses for machining metal.

2. Description of Related Art

Conventional mechanical lathes and machine tools (e.g., slitting saws) are effective for cutting metals down to approximately 100 microns kerf width at depths on the order of 1 millimeter (aspect ratio <10:1). Below this level, electron beam or laser tools are typically used for cutting or high precision machining (sculpting, drilling). Both electron beam and existing industrial laser technology remove material by a conventional thermal process where the material to be removed is heated to the melting or boiling point. Laser processing by molecular dissociation in organic (and some inorganic) materials can be achieved with excimer lasers but this photodissociation mechanism is not applicable to metals.

The basic interaction in localized thermal processing, as is achieved with electron beam or current state of the art lasers, is the deposition of energy from the incident beam in the material of interest in the form of heat (lattice vibrations). Cutting efficacy and quality may differ strongly between metals dependent upon the thermomechanical properties of the metal. Laser absorption is also dependent upon the optical properties of the metal of interest. The laser energy that is absorbed results in a temperature increase at and near the absorption site. As the temperature increases to the melting or boiling point, material is removed by conventional melting or vaporization. Depending on the pulse duration of the laser, the temperature rise in the irradiated zone may be very fast resulting in thermal ablation and shock. The irradiated zone may be vaporized or simply ablate off due to the fact that the local thermal stress has become larger than the yield strength of the material (thermal shock). In all these cases, where material is removed via a thermal mechanism, there is an impact on the material surrounding the site where material has been removed. The surrounding material will have experienced a large temperature excursion or shock often resulting in significant change to the material properties. These changes may range from a change in grain structure to an actual change in composition. Such compositional changes include oxidation (if cut in air or, in the case of alloys, changes in composition of the alloy. This affected zone may range from a few microns to several millimeters depending on the thermomechanical properties of the metal, laser pulse duration and other factors (e.g., active cooling). In many applications, the presence of the heat or shock affected zone may be severely limiting since the material properties of this zone may be quite different than that of the bulk. Furthermore, devices with features on the order of a few tens of microns cannot tolerate the thermal stress induced in the material during the machining process. Even the slightest thermal stress or shock can destroy the feature of interest.

Another limitation of conventional laser or electron beam processing in high precision applications is the presence of redeposited or resolidified material. As mentioned previously, cutting or drilling occurs by either melting or vaporizing the material of interest. The surface adjacent to the removed area will have experienced significant thermal loading often resulting in melting. This melting can be accompanied by flow prior to solidification as shown in FIG. 1A. This can result in the deposition of slag surrounding the kerf. In many high precision applications, the presence of slag is unacceptable. In the cases where the deposition of conventinal slag can be prevented, redeposition of vaporized material on the walls or upper surface of the kerf is common. This condensate often reduces the quality of the cut and decreases the cutting efficiency since the beam must again remove this condensate before interacting with the bulk material underneath. FIG. 1A shows a top view of stainless steel cut with a conventional infrared (1053 nm) laser operating at a pulse duration >1 nsec. The presence of resolidified molten material (slag) and poor single pass cut quality indicative of laser cutting by conventional methods is readily apparent.

Many of these limitations can be reduced by the use of secondary techniques to aid the cutting process. The most common of these are active cooling of the material of interest either during or immediately following the laser pulse, and the use of high pressure gas jets to remove vaporized or molten material from the vicinity of the cut to prevent redeposition. These techniques can be effective at improving the kerf at the cost of a significant increase in system complexity and often a decrease in cutting efficiency.

SUMMARY OF THE INVENTION

It is an object of the present invention to provide a method for laser cutting/machining of metals and alloys which achieves high machining speed with extreme precision, negligible heat affected zone, and no modification to the material surrounding the kerf.

The method involves the use of very short (10 femtoseconds to approximately 100 picoseconds) laser pulses delivered at high repetition rate (0.1 to over 100 kHz). Although the absorption mechanism for the laser energy is the same as in the case of long pulse lasers, the short (<100 psec) duration offers a simple and striking advantage. By adjusting the pulse duration such that the thermal penetration depth during the pulse, $L_{th}=2\alpha\Sigma$ ($\alpha=k/\rho c_p$ is the thermal diffusivity, k is the thermal conductivity, $\rho$ is the density, $c_p$ is the heat capacity and $\tau$ is the duration of the laser pulse] is less than one micron, very small amounts of material (0.01–1 micron) can be removed per laser pulse with extremely small transport of energy either by shock or thermal conduction away from the volume of interest. This offers extremely high precision machining with a negligible (submicron) heat or shock effected zone. For example, type 304 stainless steel exhibits a thermal penetration depth of only 1.5 nm for a 100 femtosecond pulse compared to an optical penetration depth of approximately 5 nm. In this case, the electric field of the laser penetrates more deeply into the steel than the thermal wave during the pulse. Hence, the depth of material removal is determined solely by the intensity and wavelength of the laser, and the absorption and heat capacity of the metal—the effects of heat conduction and thermal shock are eliminated.

The lack of significant energy deposition beyond the volume of interest achieved by using these ultrashort pulses enables the use of high repetition (0.1–100 kHz) lasers without the need for external cooling of the part being machined. Even though only a very small depth of material is removed per pulse, the high repetition rate enables extremely high cut rates (beyond 1 mm depth per second).

Cut quality and cut efficiency with these ultrashort pulses can be significantly higher than that achievable for conventional long pulse lasers. This follows from two critical features: 1) there is little loss of energy away from the region of interest since thermal conduction during the pulse is negligible and 2) there is no vaporization or transport of material during the pulse. The second of these features may require additional explanation. During the pulse, there is insufficient time for hydrodynamic expansion of the vaporized material. As a result, the laser pulse encounters the solid surface for the duration of the pulse, depositing energy into the solid density material and raising a depth to a temperature far beyond the boiling point (typically to temperatures above the ionization point). After the pulse is over, the depth which has been raised above the boiling point leaves the surface with an expansion velocity determined by the initial temperature. Typical temperatures in the expanding plasma are between 1 and 100 eV and are determined by the product of the incident laser irradiance, $I(W/cm^2)$ and square of the laser wavelength, $\lambda^2(\mu m)$. The high plasma temperature insures that the vaporized material will be completely removed from the kerf without redeposition on the walls. This material is removed before the arrival of the next laser pulse 0.01 to 10 milliseconds later. For example, an expanding vapor with even a low expansion velocity of $10^5$ cm/sec will be 1 meter away from the surface before the arrival of the next pulse if operating at a 1 kilohertz repetition rate. With conventional nanosecond or microsecond lasers, the vapor will evolve during the laser pulse. This reduces the coupling of the laser light to the solid surface since the incident laser light will be scattered and absorbed by the vapor. This problem is completely overcome by the use of the very short pulses of the present invention.

High precision machining of metals is an extremely large industry world-wide. This industry continues to grow with new applications particularly in semiconductor processing and display technology appearing frequently. Conventional mechanical lathes and machine tools are effective for cutting applications down to approximately 100 microns kerf width. Below this level, electron beam or laser tools are typically used for cutting or high precision machining (sculpting, drilling). Both electron beam and existing industrial laser technology remove material by a conventional thermal process where the material to be removed is heated to the melting or boiling point. The temperature of the surrounding material is determined by standard heat conduction from the region of interest. While small scale features (<100 microns) are readily achieved, they are often surrounded by resolidified material (slag) and by a significant heat affected or shock zone often requiring post processing (e.g., annealing, electro-polishing, etc.). This heat affected zone alters the properties of the material in the vicinity of the machined surface, often resulting in reduced material strength or modification of the composition of the material in the case of alloys. The present invention converts the region to be removed from the solid-state to the plasma state so quickly that there is insufficient time for significant heat transfer beyond the depth of material removed. This results in the ability to perform extremely high precision machining of metals or alloys with essentially no heat affected zone and eliminates the need for cooling of the part during the machining process. Hydrodynamic expansion of the plasma eliminates the need for any ancillary source to aid in material removal such as gas flow.

This invention enables, but is not limited to, applications requiring high precision (<100 microns) or remote machining (cutting, drilling or sculpting) with no change in the remaining material (grain structure, alloy composition, materials strength, etc.). Specific examples include the production of microgears and valves, insertable medical devices and disk patterning.

DETAILED DESCRIPTION OF THE INVENTION

The invention covers a method of machining (cutting, drilling or sculpting) metals and alloys by focusing a laser pulse with a duration of between 10 femtoseconds to as long as 100 picoseconds onto the surface of the material of interest in such a manner as to produce an ionized plasma on the surface while all material to a depth beyond approximately 1 micron from the interaction point is substantially unaffected by the removal of the ablated material (in some metals, this distance can be less than 0.1 microns). Any laser system capable of producing a focused irradiance greater than $10^{12}$ $W/cm^2$ in a duration from 10 femtoseconds to approximately 100 picoseconds can be used in the method. Any wavelength laser source can be used provided the beam is focused to achieve a peak irradiance ($Watts/cm^2$) high enough to produce an ionized plasma.

Figure 1A:
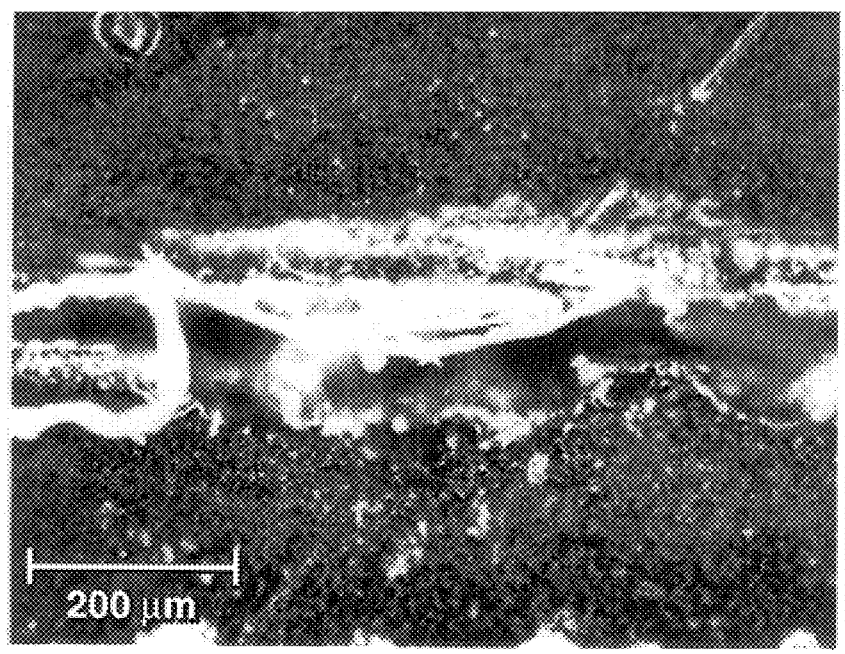
FIG. 1A shows a top view of stainless steel cut with a conventional infrared (1053 nm) laser operating at a pulse duration >1 nsec.
Figure 1B:
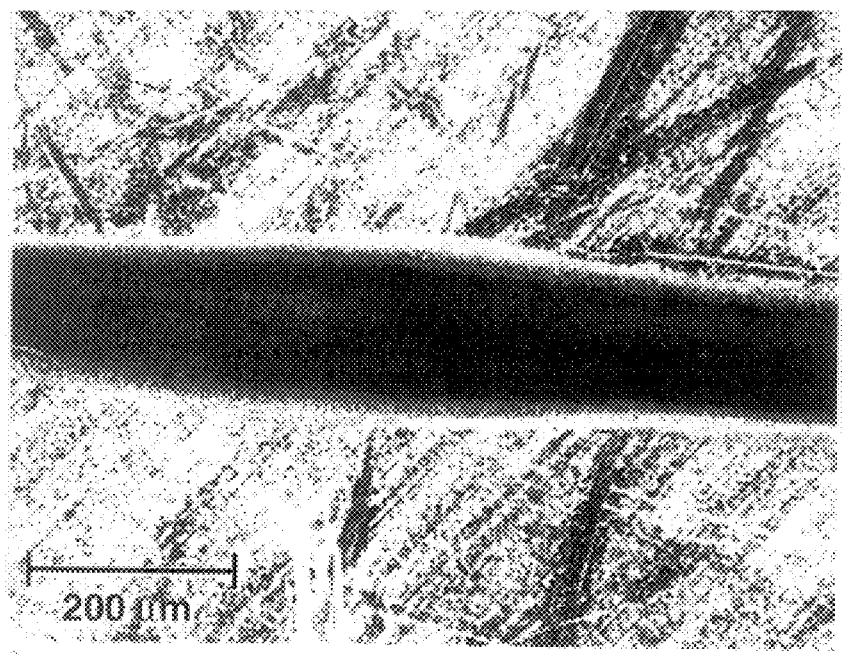
FIG. 1B shows a top view of stainless steel, as in FIG. 1A, but cut with the method of the present invention.

An embodiment of the laser system of the present invention produces a pulsed output beam having a selectively variable pulse duration from about 30 femtoseconds to over 100 picoseconds at a variable pulse repetition rate from 1 Hertz to over 2 kilohertz. The energy per pulse obtainable from the laser system is variable from 1 microjoule to over 5 millijoules (at repetition rates <2 kHz) deliverable in a beam having a spot size variable from about 3 microns to over 1 centimeter. These parameters have been shown to be particularly effective in ablating all types of materials. FIG. 1B shows a top view of stainless steel, as in FIG. 1A, but cut with the method of the present invention. The pulse duration was 350 femtoseconds and the laser wavelength was 1054 nm. The fluence on the steel surface was 14 $J/cm^2$ corresponding to an irradiance of $4 \times 10^{13}$ W/cm². There is no evidence of melting or slag. The surface quality of the cut is better than achievable with conventional mechanical methods in the absence of post polishing.

Figure 2A:
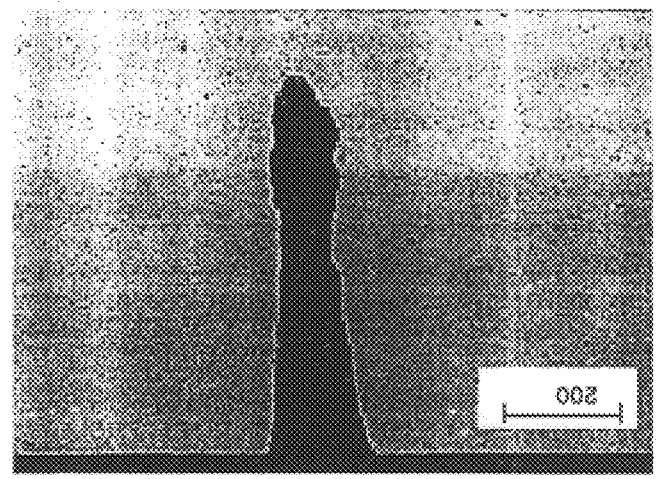
FIG. 2A shows a side view of aluminum cut with a conventional visible (532 nm) laser operating at a pulse duration >8 nsec.
Figure 2B:
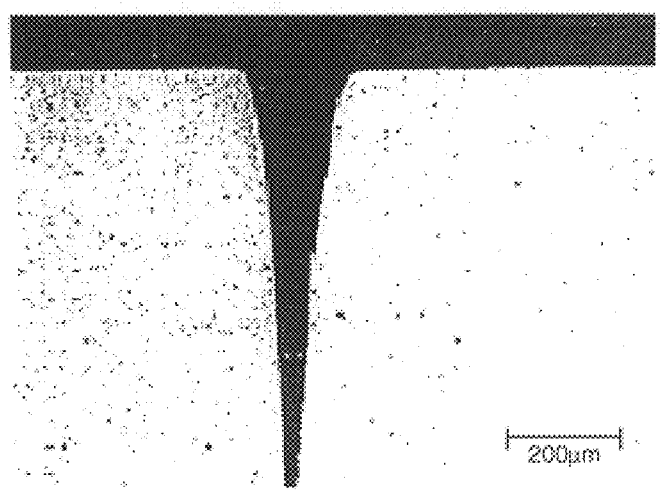
FIG. 2B shows a side view of aluminum cut with the method of the present invention.

FIG. 2A shows a side view of a piece of aluminum that has been cut with a conventional visible (532 nm) laser operating at a pulse duration less than 8 nsec. It can be seen from the figure that a heat affected zone extends into the material beyond the kerf. This heat affected zone modifies the grain structure of the material and results in poor cut quality. FIG. 2B shows a side view of a piece of aluminum that has been cut with the method of the present invention. The pulse duration was 350 femtoseconds and the laser wavelength was 1054 nm. The fluence on the steel surface was ≈6 J/cm² corresponding to an irradiance of ≈$2 \times 10^{13}$ W/cm². There is no evidence of melting or slag. There is no evidence of a heat or shock affected zone and the grain structure of the bulk material is maintained to less than 0.5 microns from the kerf.

Although, as will be described in greater detail below, any type of laser system, capable of operating within the parameters described above, can be employed in practice of the invention, the laser system preferably begins with a mode-locked oscillator 10, as shown in block form in FIG. 3, for producing pulses of either the same or shorter duration than the final desired pulse duration. Commercial oscillators producing 100 femtosecond pulses are usable in accordance with the present invention. Another usable laser system disclosed herein is a custom built oscillator producing 20 femtosecond pulses. The oscillators utilize Titanium-doped sapphire as the laser material and utilize the Kerr effect for mode-locking. However, any laser material and modelocking mechanism capable of producing pulses of the desired duration can be employed. The pulses produced from these oscillators are very low in energy, on the order of 1 nanojoule. These low energy pulses are stretched in time prior to amplification by a factor of over one thousand.

Pulse stretching prior to amplification is necessary so as to avoid damaging the laser amplifiers by the intense pulse. This stretching is achieved by passage of the pulse through a dispersive optical device 12. A dispersive optical device is one in which the time required to traverse the device is a function of the frequency of the light. This is most commonly achieved by devices in which the optical path length is a function of frequency. Examples include propagation through a fiber where the variation in optical path length with frequency, ω, is given by the frequency dependence of the refractive index, $n(\omega)$, i.e., $L_{opt} = n(\omega) L_{fiber}$. Much higher dispersion can be achieved with pulse stretchers employing a diffraction grating where the different frequency components of the laser pulse travel physically different paths determined by the angular dispersion of the grating, $m\lambda = \sin(\theta_{in}) + \sin(\theta_{out})$, where λ is the wavelength of the laser light and $\lambda_{in}$ and $\lambda_{out}$ are the input and output angles from the diffraction grating, respectively. In the present system, a device employing a 1800 grooves/mm diffraction grating, a 1 meter focal length concave spherical mirror and a pair of retro-reflecting roof mirrors stretches the pulse from 100 fsec to approximately 500 psec, to achieve a stretching ratio of ≈5000.

The stretched pulse is amplified by several orders of magnitude to the millijoule level in the next stage. Although many types of laser amplifiers could be used here, as shown in FIG. 3, the preferred embodiment is a regenerative amplifier 14. This is a device wherein the pulse can make multiple passes through a single amplifier media. The regenerative amplifier used in this embodiment utilizes Titanium-doped sapphire as the gain medium. However, any laser material with sufficient bandwidth to support the bandwidth of the short pulse may be used. Specific laser materials used by the inventors include Chromium-doped $LiSrAlF_6$, Neodymium-doped glass, Neodymium-doped yttrium aluminum garnet (Nd:YAG), Neodymium-doped yttrium lithium fluoride (Nd:YLF) and Ytterbium-doped Yttrium aluminum garnet (Yb:YAG).

Figure 3:
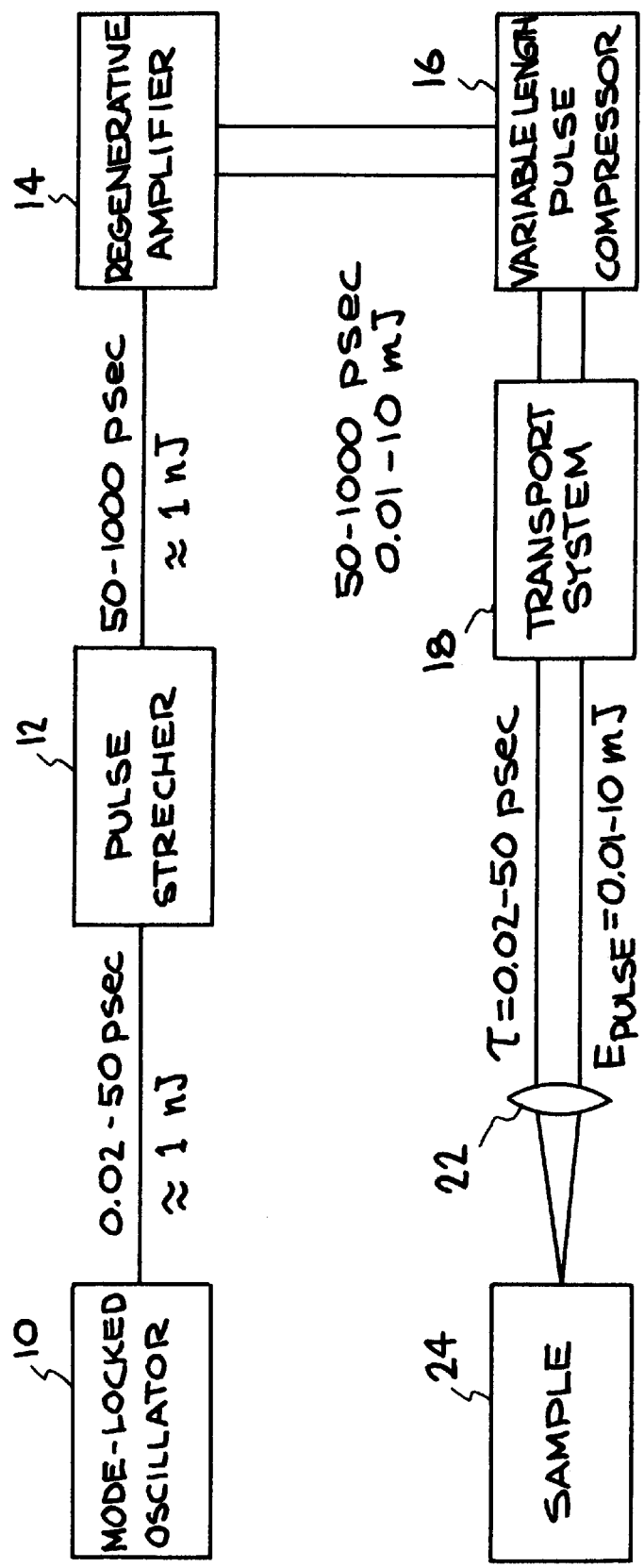
FIG. 3 shows a block diagram of a laser usable in the present invention.

In the system shown in FIG. 3, a second laser is used to pump the Ti:sapphire gain medium due to the short upper-state lifetime of Ti:Sapphire. Both a frequency-doubled, Q-switched Neodymium-yttrium-lithium-fluoride (Nd:YLF) laser or a Nd:YAG laser have been used as the pump laser. The energy required to pump the Ti:sapphire regenerative amplifier is typically greater than four times the energy output of the regenerative amplifier. The repetition rate of this system is determined by the repetition rate of the pump laser. Continuous pumping of the Ti:Sapphire gain medium in the regenerative amplifier has also been demonstrated. In this case, the repetition rate of the system is determined by the optical switching within the regenerative amplifier. Switching of the pulse into and out of the regenerative amplifier is accomplished with optical pulse switching technology based on the Pockels or acousto-optics effects. The regenerative amplifier 14 produces pulses up to 8 mj in energy. Following amplification, the pulse is compressed by a variable length pulse compressor 16 employing a diffraction grating. The inventors have demonstrated a final pulse duration which can typically be adjusted between 30 femtoseconds and 100 picoseconds. The pulse energy exiting the grating compressor 16 is reduced by approximately 30 percent from that exiting the regenerative amplifier 14 as a result of the diffraction efficiency of the grating.

The method of producing high peak power ultrashort pulses where the initial short pulse is stretched prior to amplification, amplified and then recompressed is known to those skilled in the art as chirped-pulse amplification.

Referring still to FIG. 3, the laser pulse is directed to the focusing system by a delivery system 18 such as an open beam transport system, an articulated arm, an optical fiber or hollow core waveguide. The delivery system 18 may be designed to provide additional compression of the pulse duration. The beam transport is comprised of standard relay telescopes which are well known in the art. The focusing system is comprised of either a simple or compound lens 22 or concave mirror arrangement for focusing the pulse onto the target material 24 with the desired kerf width.

Figure 4:
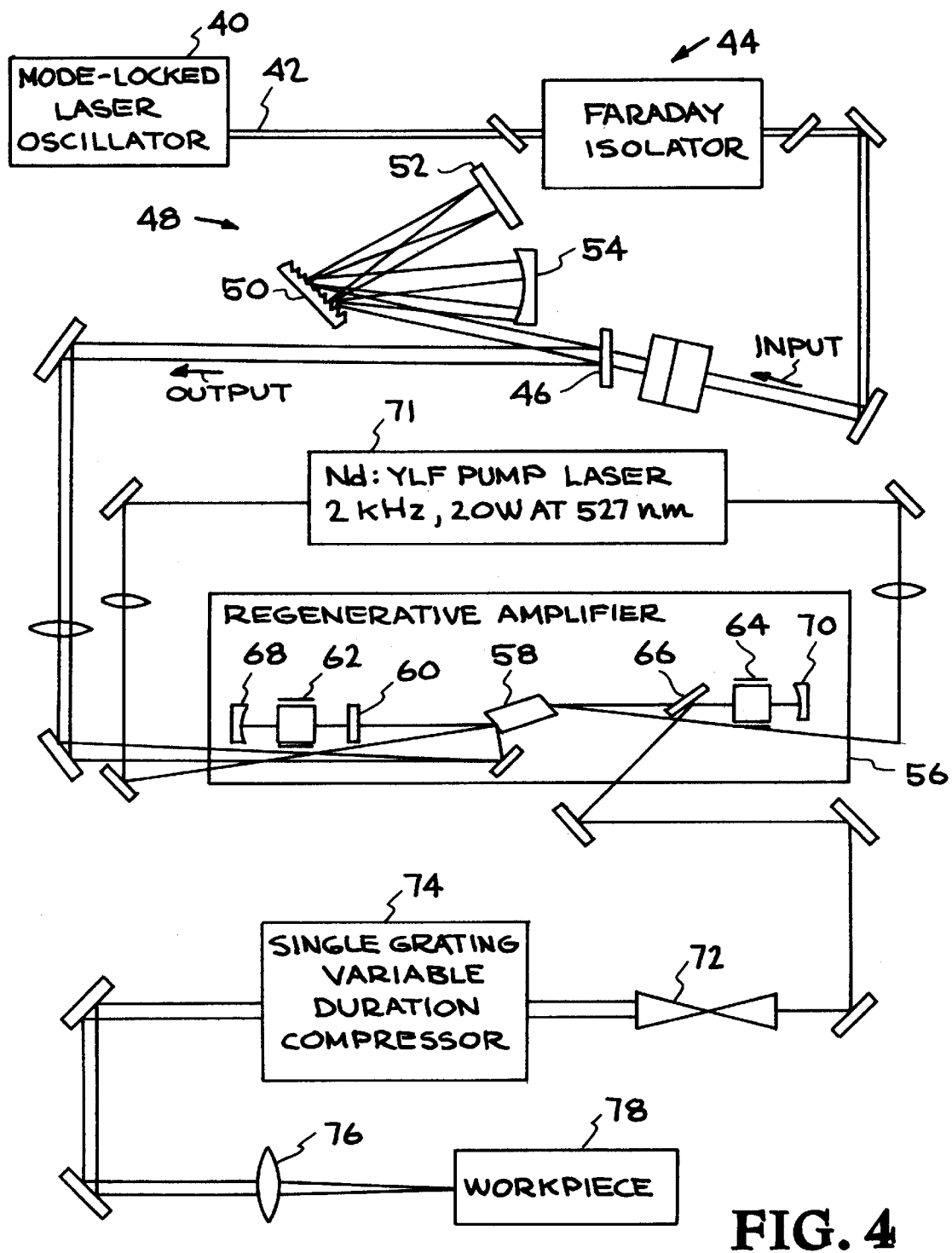
FIG. 4 shows an exemplary laser system usable in the present invention.

Referring to the exemplary laser system of FIG. 4, a mode-locked laser oscillator 40 produces 100 fsec pulses having an average power of less than 1 Watt at 76 MHz and traveling on beam path 42. Faraday isolator 44 prevents amplified light from reaching oscillator 40. The pulses traveling on beam path 42 pass through pick-off mirror 46 and into pulse stretcher 48, which consists of an 1800 l/mm grating 50, a flat mirror 52 (in the Fourier plane) and a spherical mirror 54. The pulses exiting the pulse stretcher 48 are focused into regenerative amplifier 56, which consists of a Ti:Sapphire medium 58, λ/4 wave plate 60, Pockels cells 62, 64, thin film polarizer 66 and 5 meter concave cavity mirrors 68, 70. The Ti:Sapphire medium 58 is optically pumped by an Nd:YLF pump laser 71 operating at 2 kHz, 20 Watts and 527 nm. Firing of the first Pockels cell to quarter-wave voltage (≈3500 V) combined with the λ/4 wave plate 60 switches a single pulse from the 76 MHz pulse train into the regenerative amplifier. After making approximately 20 passes through the Ti:Sapphire medium 58, the pulses are ejected from the regenerative amplifier cavity by firing the second Pockels cell to quarter-wave voltage. A double-pass through this Pockels cell rotates the beam polarization by 90 degrees whereupon the pulse is then directed out of the cavity by the thin film polarizer. Following the regenerative amplifier, the pulse is directed to a single grating compressor 74 by standard beam transport optics 72. It is then focused with an achromatic lens 76 having a 30 cm focal length onto a workpiece 78. The irradiance at the workpiece for this system will exceed $10^{13}$ W/cm$^2$.

Figure 5:
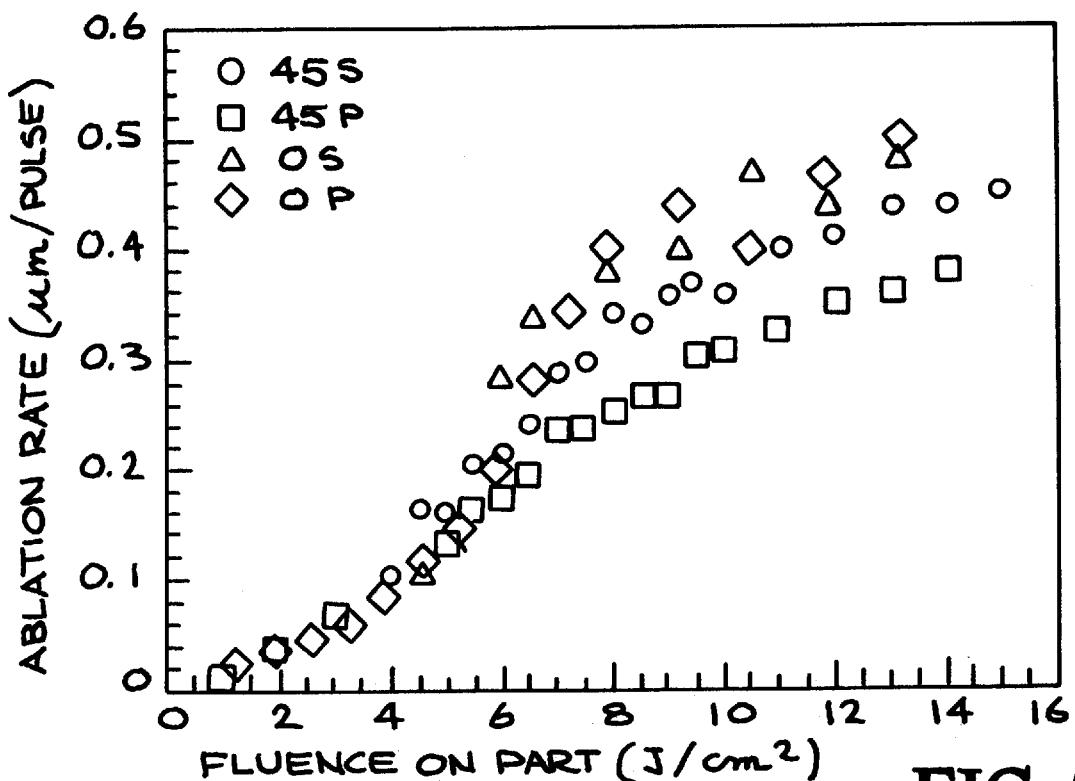
FIG. 5 shows depth of stainless steel material removed per pulse as a function of laser fluence for 120 fsec pulse duration.

Central to the present invention is that the focusing conditions must achieve the threshold irradiance to initiate plasma formation. Typical values are approximately $10^{14}$ W/cm$^2$ for 100 fsec pulses. This is illustrated in FIG. 5 where the depth of material removed per pulse is shown as a function of laser fluence (J/cm$^2$) for 120 fsec pulses in stainless steel. The data was taken in the limit of no waveguide effects (140 micron thick stainless steel). The figure insert refers to the angle of incidence of the beam and polarization. The figure shows that there was low ablation until the laser fluence exceeded about 5 J/cm$^2$ on the part. Below approximately 4 J/cm$^2$, very low cut rates are achieved. The depth of material removed per pulse rises quickly between 4 and 10 J/cm$^2$ to a value of approximately 0.4 mm per pulse. The cut depth then saturates for all polarizations and no longer increases beyond 15 J/cm$^2$. In the saturated regime and beyond, any further increase in laser irradiance goes towards increasing the temperature of the plasma with little effect on the cut rate for thin samples. The spot size is easily adjusted either by moving the target away from best focus or by changing the focusing element. All of these focusing techniques are well known to those skilled in the art.

Figure 6:
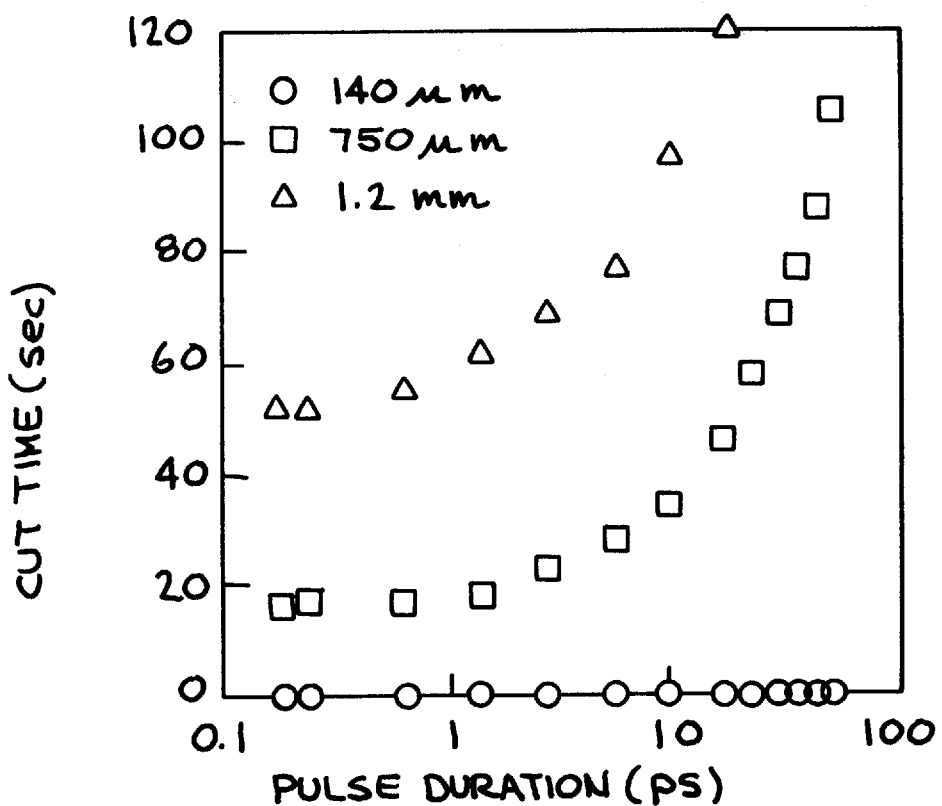
FIG. 6 shows the time required to cut through stainless steel of various thickness as a function of pulse duration at a fixed fluence of 12 $J/cm^2$.

When cutting thick material at high aspect ratio (thin kerf in thick material, (e.g., 50 micron kerf in 1 mm thick steel), an irradiance beyond the saturation level is often required to achieve sufficiently high plasma temperature to prevent redeposition on the kerf. This is due to two factors. First, in high aspect ratio cutting, the kerf itself may function as a waveguide. This both reshapes the spatial distribution of the laser light and reduces the intensity reaching the bottom of the kerf. As a result, the fluence incident on the bottom of the kerf may be substantially less than that incident on the part surface. Second, as the plasma expands from the surface, it cools. The irradiance at the bottom of the kerf must be sufficiently high to insure a high enough temperature such that when the plasma expands and cools, it cannot cool to the point where it can condense on the walls of the kerf as it exits. This high irradiance can be achieved either by shortening the pulse duration at a fixed fluence or by increasing the fluence for a fixed duration. FIG. 6 shows the time required to cut through stainless steel of various thickness as a function of pulse duration at a fixed fluence of 12 J/cm$^2$. The pulse repetition rate of the laser was 1 kHz. For the thicker materials, the figure shows a dramatic improvement in cut time as the pulse duration is shortened.

Any laser wavelength from 0.25 to over 10 microns can be used in the present invention. The laser used in the reduction to practice can produce continuously tunable output from approximately 780 to over 1000 nanometers (nm) by a simple change of optics and minor adjustments to the angles of the gratings in the pulse stretcher and compressor. In order to optimize the cutting efficiency for particular metals, the system can be operated in the 400 to 500 nm range by conversion to the second harmonic. Operation at the second harmonic (400 to 500 nm) is accomplished by passing the beam through a thin nonlinear crystal (e.g., potassium di-hydrogen phosphate (KDP), Lithium Borate, b-Barium borate, etc.) after compression. The crystal can be cut for either type I or type II phase matching and is typically between 0.1 and 4 millimeters in length.

Changes and modifications in the specifically described embodiments can be carried out without departing from the scope of the invention, which is intended to be limited by the scope of the appended claims.

What is claimed is:

1. A method for machining metals and alloys, comprising:

producing a pulsed laser output beam from a solid state laser, wherein said pulsed laser output beam comprises a plurality of laser pulses wherein said laser pulses have a pulse repetition rate greater than 10 Hz and a wavelength in the range of 750 nm to 10.7 microns, wherein each pulse of said plurality of laser pulses has a pulse duration of 100 picosecond or less; and directing said pulsed laser output beam onto a workpiece comprising metal or alloy, wherein each said pulse converts approximately greater than 0.1 micron to 1 micron of material of said workpiece from a solid state to a plasma state, wherein said material is removed from said workpiece by hydrodynamic expansion of said plasma.

2. A method for machining metals and alloys, comprising:

producing a laser beam from a solid state laser; and directing said laser beam onto a workpiece comprising material selected from a group consisting of metal and alloy, wherein said laser beam comprises a plurality of laser pulses, wherein said laser pulses have a pulse repetition rate greater than 10 Hz and a wavelength in the range of 750 nm to 10.7 microns, wherein each said pulse has a pulse duration within the range of 10 femtoseconds to 100 picoseconds and a focused irradiance of greater than $10^{12}$ W/cm$^2$, wherein each pulse of said plurality of laser pulses converts approximately greater than 0.1 micron to 1 micron of material of said workpiece from a solid state to a plasma state, wherein said material is removed from said workpiece by hydrodynamic expansion of said plasma.

3. The method of claim 2, wherein said plurality of laser pulses removes said material from said workpiece with no modification of or damage to the structure of remaining material of said workpiece beyond approximately 1 micron from the kerf.

4. The method of claim 2, wherein said plurality of laser pulses removes material with no modification of or damage to the structure of remaining material of said workpiece beyond a depth within a range of approximately 0.1–1 micron, depending upon a particular type of material, wherein said range of said depth of said modification of or said damage to said structure is dependent upon said particular type of said material.

5. The method of claim 2, wherein said pulse duration is adjusted such that the thermal penetration depth $L_{th}$ during each pulse, which is equal to $2\sqrt{\alpha\tau}$, where $\alpha=k/\rho c_p$ is the thermal diffusivity, k is the thermal conductivity, $\rho$ is the density, $c_p$ is the heat capacity and $\tau$ is the duration of the laser pulse, is less than one micron.

6. The method of claim 2, wherein the electric field of each said pulse penetrates more deeply into said material than a thermal wave produced in said material during each said pulse.

7. The method of claim 2, wherein said plurality of laser pulses removes said material from said workpiece with no modification of or damage to the structure of remaining material of said workpiece beyond approximately 1 micron from the kerf, wherein external cooling of said workpiece is unnecessary.

8. The method of claim 2, wherein said method produces a minimum cut rate that is at least 1 mm depth per second.

9. The method of claim 5, wherein each said pulse converts said material from the solid-state to the plasma state so quickly that there is insufficient time for the production of heat transfer that would be damaging to said material beyond the depth removed from said material, wherein as each said pulse encounters the solid surface of said material for the duration of said pulse, energy is deposited into said material to raise a depth of said material to a temperature beyond its boiling point, typically to temperatures above the ionization point, wherein after said pulse is over, said depth leaves the surface of said material with an expansion velocity determined by the initial temperature of said depth of said material.

10. An apparatus for machining metals and alloys, comprising:

a solid state laser for producing a pulsed laser output beam comprising a plurality of laser pulses wherein said laser pulses have a pulse repetition rate greater than 10 Hz and a wavelength in the range of 750 nm to 10.7 microns, wherein each said pulse of said plurality of laser pulses has a pulse duration of 100 picosecond or less; and means for directing said pulsed laser output beam onto a workpiece comprising metal or alloy, wherein each said pulse converts approximately greater than 0.1 to 1 micron of material of said workpiece from a solid state to a plasma state, wherein said material is removed from said workpiece by hydrodynamic expansion of said plasma.

11. An apparatus for machining metals and alloys, comprising:

a solid state laser for producing a laser beam: and means for directing said laser beam onto a workpiece comprising material selected from a group consisting of metal and alloy, wherein said laser beam comprises a plurality of laser pulses, wherein said laser pulses have a pulse repetition rate greater than 10 Hz and a wavelength in the range of 750 nm to 10.7 microns, wherein each said pulse of said plurality of laser pulses has a pulse duration within the range of 10 femtoseconds to 100 picoseconds and a focused irradiance of greater than $10^{12}$ W/cm$^2$, wherein each pulse of said plurality of laser pulses converts approximately greater than 0.1 micron to 1 micron of material of said workpiece from a solid state to a plasma state, wherein said material is removed from said workpiece by hydrodynamic expansion of said plasma.

* * * * *